(12) United States Patent
Habermehl et al.

(10) Patent No.: US 9,080,951 B2
(45) Date of Patent: Jul. 14, 2015

(54) METHOD AND SYSTEM OF USING 1.5D PHASED ARRAY PROBE FOR CYLINDRICAL PARTS INSPECTION

(71) Applicants: Jason Habermehl, Quebec (CA); Jinchi Zhang, Quebec (CA)

(72) Inventors: Jason Habermehl, Quebec (CA); Jinchi Zhang, Quebec (CA)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 357 days.

(21) Appl. No.: 13/853,764

(22) Filed: Mar. 29, 2013

(65) Prior Publication Data

US 2013/0283918 A1 Oct. 31, 2013

(51) Int. Cl.
*G01N 29/26* (2006.01)
*G01N 29/06* (2006.01)
*G01N 29/265* (2006.01)

(52) U.S. Cl.
CPC .............. *G01N 29/26* (2013.01); *G01N 29/069* (2013.01); *G01N 29/262* (2013.01); *G01N 29/265* (2013.01); *G01N 2291/106* (2013.01); *G01N 2291/2634* (2013.01)

(58) Field of Classification Search
CPC ................ G01N 29/26; G01N 29/265; G01N 2291/2634; G01N 29/069; G01N 29/262; G01N 2291/106
USPC .......................................................... 73/622
See application file for complete search history.

(56) References Cited

U.S. PATENT DOCUMENTS

| | | | | |
|---|---|---|---|---|
| 6,524,254 | B2 * | 2/2003 | Erikson ......................... | 600/447 |
| 6,789,427 | B2 * | 9/2004 | Batzinger et al. ............... | 73/614 |
| 6,813,950 | B2 * | 11/2004 | Glascock et al. ............... | 73/633 |
| 7,338,450 | B2 * | 3/2008 | Kristoffersen et al. ........ | 600/447 |
| 7,431,698 | B2 * | 10/2008 | Bruestle ........................ | 600/459 |

\* cited by examiner

*Primary Examiner* — J M Saint Surin
(74) *Attorney, Agent, or Firm* — C. Tricia Liu

(57) ABSTRACT

A method of using a 1.5D array ultrasonic probe as a component of an inspection system intended for different diameter cylindrical parts without mechanical adjustments of the probe is presented. In particular, the method is presented as a way to improve the near surface resolution over an extended range of cylindrical parts diameter and inspection depths/tubes wall thickness with respect to usual 1D arrays of fixed curvature along the elevation axis. The method relies on a customizable concentric firing pattern of the acoustic pulses with respect to the cylindrical part surface, and on adjustment of the aperture size of the said array. The intended effect is to sharpen and minimize the extent of the front wall echo and to optimize the response from an eventual flaw in the inspected range.

6 Claims, 5 Drawing Sheets

METHOD AND SYSTEM OF USING 1.5D PHASED ARRAY PROBE FOR CYLINDRICAL PARTS INSPECTION

FIELD OF THE INVENTION

The present invention relates to the field of industrial non-destructive testing and inspection (NDT/NDI) and in particular to a method of using a bi-dimensional phased array ultrasound probe for the characterization and flaw detection of seamless cylindrical products such as pipes and round bars.

BACKGROUND OF THE INVENTION

For any user or manufacturer of cylindrical products such as tubes or bars, it is a common practice to inspect the parts for the diagnosis of variations in the wall thickness and the presence of flaws in the base material. For this purpose, ultrasonic inspection techniques have become a recognized standard in the industry. With such techniques, it is customary to employ a transducer to apply high-frequency acoustic energy into the cylindrical part to be tested. The high-frequency acoustic field is first pulsed through a coupling medium and into the inspected part. As the acoustic wave propagates through the tested part, it gets scattered by the encountered inhomogeneity and discontinuities of the material. A fraction of the acoustic field is consequently reflected back to a receiving transducer which detects the incoming acoustic field echo. The material characteristics along the sound path, such as wall thickness and possible flaws, are deduced by monitoring this returning signal.

A new paradigm was formed in the field of nondestructive testing with the introduction of phased array (PA) multi-elements ultrasonic technology to enhance the performance of conventional ultrasonic single element probe inspection systems. A general description of how phased array technology can be adapted to imaging systems is given in U.S. Pat. No. 5,563,346 with recent examples of applications for the inspection of spherically bounded materials and turbine blades described in U.S. Pat. Nos. 6,279,397 and 6,082,198 respectively.

Another application of phased array technology precisely amounts for the inspection of cylindrical parts during production. In order to ensure complete coverage of the concerned parts, it is necessary to place PA probes at positions that allow reaching the entire circumference of the cylindrical product. This may be accomplished either by placing the PA probes all around a non-rotating cylindrical part, or by having a rotating part to roll in front of a fixed PA probe. Typical phased array industrial inspection systems for rotating cylindrical parts currently comprise linear phased array probes that increase productivity significantly compared to conventional ultrasound systems. However, despite the obvious advantages of linear phased array probes with respect to primary axis electronic scanning and focusing, these probes lack the flexibility to provide optimal inspection results on a large range of tube and bar diameters and thicknesses without the need of changing either the PA probes or the probe holders. On one hand, changing these components between inspection cycles adds downtime and inactive equipment costs. On the other hand, employing a non-optimal phased array probe and probe holder for a given inspection results in poor signal to noise ratio levels and diminished near-surface resolution.

One group of existing efforts has relied on a PA probe that possesses ultrasound element spanning both the scan and elevation axes in the form of a bi-dimensional matrix. While the N columns of elements on the scan axis (primary axis) may be individually electronically addressed to allow for beam steering and focusing, the M rows of elements along the elevation axis (secondary axis) of a given column are connected in symmetrical pairs; in the following, the number of rows is assumed to be odd. This configuration, known in the art as 1.5 D array (see U.S. Pat. Nos. 5,490,512 and 6,089,096 for instance), obviously restrains the beam manipulation freedom along the elevation axis. Yet, the figure of merit of the 1.5 D array rests in its ability to form custom electronically focused beams along an otherwise passive axis while requiring only $(M+1)/2 \times N$ electronic leads instead of $M \times N$ for a full 2 D array. It also permits the active control of the aperture size for field optimization as described in U.S. Pat. No. 5,846,201.

Another existing practice is known in the art to increase the signal to noise ratio of eventual flaws inside the inspection range. The optimal choice of aperture size may be drawn from empirical results or numerical simulations for instance. The preferred embodiment of the method is especially suited for the inspection of tubular parts, but may be used for the near surface inspection of whole cylindrical bars. This adapted aperture procedure is similar to the one found in U.S. Pat. No. 5,490,512.

Yet in another existing practice, the firing pattern is made concentrically to the cylindrical part. This configuration ensures that the pulsed acoustic field from each elemental transducer reaches the surface of the part with the same minimum time, thus minimizing the extent of the front wall echo and sharpening its boundaries. This type of firing setup is similar to the one found in US Patent Application No. 2006/0195273.

Accordingly, the objective of the present invention is to provide a method for inspecting an extended range of tube and bar diameters and thicknesses with a single probe and probe holder that provides the advantages of improved near-surface resolution (herein later also as NSR) and improved signal to noise ratio by exploiting the benefits of a 1.5 D phased array probe.

SUMMARY OF THE INVENTION

The present invention provides a method of using a 1.5 D probe to improve the range of cylindrical part diameters that may be adequately inspected in the near-surface area without changing either the PA probe or the distance separating the probe from the inspected part.

The present method provides means of activating specific series of elements of a 1.5 D array both in transmission and reception. The acoustic field emitted from the transducer array is produced by the excitation of piezoelectric elements with properly delayed electronic pulsed signals. This method is known in the art to form custom acoustic beams. A preferred embodiment of the method uses sequential yet independent activation of the N individual columns of elements along the scan axis and applies specific delayed signals only on the $(M+1)/2$ leads of the elevation axis of a given column. Consequently, the preferred embodiment produces user-defined beams along the elevation axis only. The electronic customization of beams along both the secondary and the primary axes using a superposition of beams from columns of elements satisfying the preferred embodiment of the method for a single column of elements is perceived as another embodiment of the same method. For instance, in such another embodiment, individual columns of elements could be electronically controlled as to satisfy the preferred embodiment while series of such columns could be controlled along the primary axis like in regular uni-dimensional PA to allow for electronic steering and focusing.

The preferred embodiment adopts an aforementioned prior-art method for optimizing the near-surface resolution of cylindrical parts given a constant probe-to-part distance. On one hand, the array is operated by activating the row transducers of a given column in such a way that the pulsed field from each transducer arrives simultaneously at the surface of the cylindrical part. In other words, the firing pattern is concentrical to the cylindrical part. This configuration ensures that the pulsed acoustic field from each elemental transducer reaches the surface of the part with the same minimum time, thus minimizing the extent of the front wall echo and sharpening its boundaries. This type of firing setup is similar to the one found in US Patent Application No. 2006/0195273, as mentioned in the BACKGROUND.

Then, the size of the aperture along the elevation is chosen as to increase the field intensity within a predefined range of inspection of the cylindrical part. This practice is known in the art to increase the signal to noise ratio of eventual flaws inside the inspection range. The optimal choice of aperture size may be drawn from empirical results or numerical simulations for instance. The preferred embodiment of the method is especially suited for the inspection of tubular parts, but may be used for the near surface inspection of whole cylindrical bars. This adapted aperture procedure is similar to the one found in U.S. Pat. No. 5,490,512.

An important novel aspect of the preferred embodiment rests in the combination of the concentric firing pattern and the aperture adaptation for the near-surface inspection of cylindrical parts. With respect to one-dimensional arrays of fixed curvature along their elevation axis, the use of the 1.5 D array grants an extended range of bar diameters that may be optimally inspected without changing the probe-to-surface distance or the probe itself. Together with the ability to adjust the field intensity distribution, the preferred embodiment also provides a way to increase the signal to noise ratio of eventual flaws within the inspected area. This property is especially suited for the inspection of orders of tubes of different wall thickness without changing the mechanical configuration of the inspection system.

Another embodiment of the method could include the synchronized firing of many such adapted columns of transducers in order to produce focused and steered beams along the scan axis.

BRIEF DESCRIPTION OF THE DRAWINGS

The drawings presented are not necessarily to scale. Emphasis is placed upon illustrating the principles of the preferred embodiment of the method.

DETAILED DESCRIPTION OF THE PREFERRED EMBODIMENT

The method proposed by the preferred embodiment is presented from a hierarchical high level-low level perspective.

Figure 1:
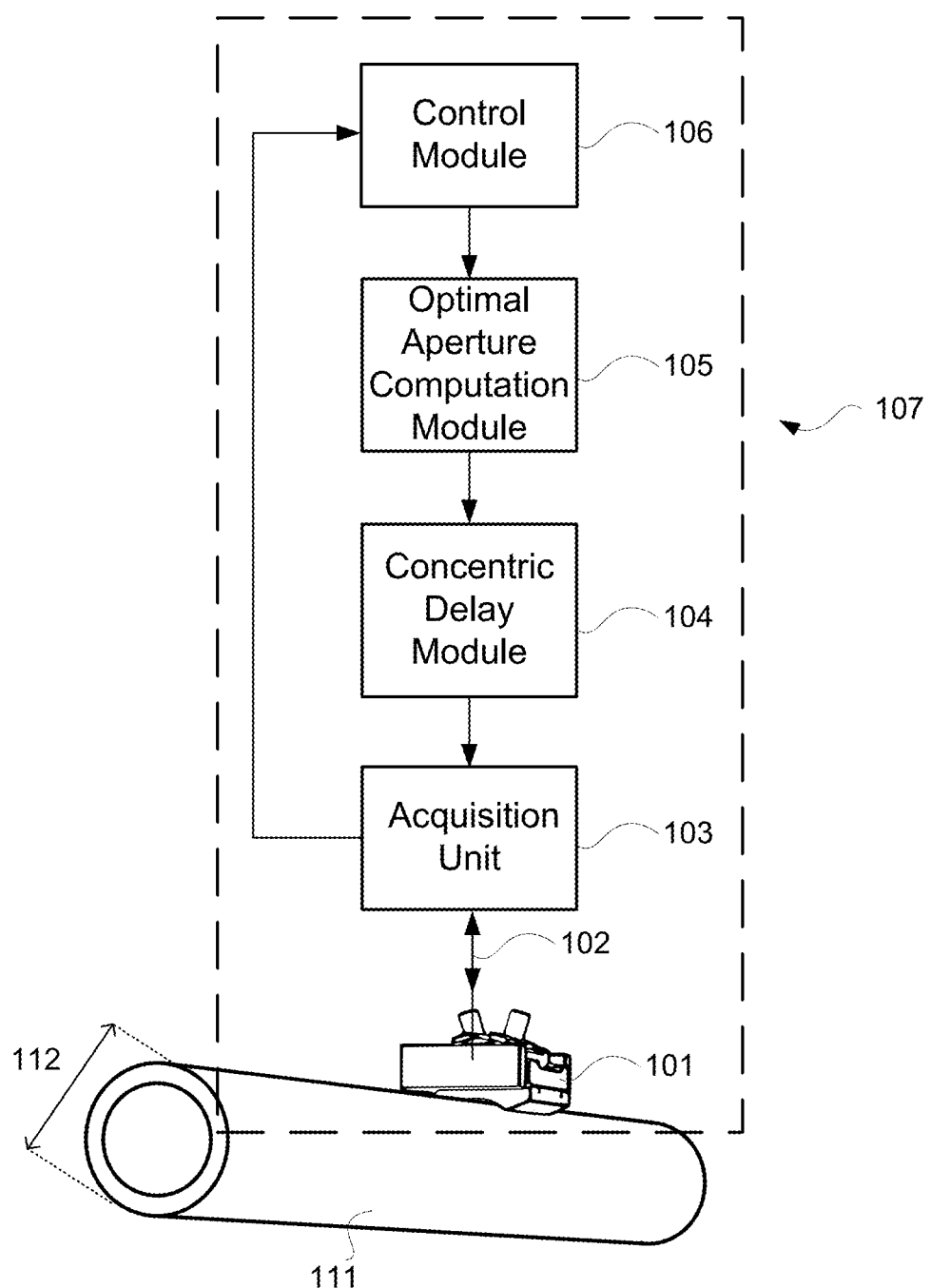
FIG. 1 is a schematic of a cylindrical parts inspection system including modules for computing the optimal aperture size and preparing the delay-based concentric firing pattern.

In FIG. 1, a conceptual view of a subset of an inspection system for cylindrical parts is shown. The depicted cylindrical part 111 is a tube of outer diameter 112. The complete inspection system 107 provides a way to rotate the cylindrical part with respect to the probes for complete coverage by the PA probes. A control module 106 directs the appropriate cylindrical part parameters and inspection range to an aperture optimization module 105 that optimizes through computation the aperture size along the elevation axis according to the intended inspection parameters. The optimal aperture parameters are then sent to a concentric delay module 104 that readies the delay-based concentric firing pattern for the computed aperture. The prepared focal law is then inputted in the acquisition unit 103 that serves as a two-way input-output 102 device for enabling ultrasound emission and reception from PA probes located inside a probe holder 101. The received inspection data is then sent back to the control module 106 for further processing.

Figure 2:
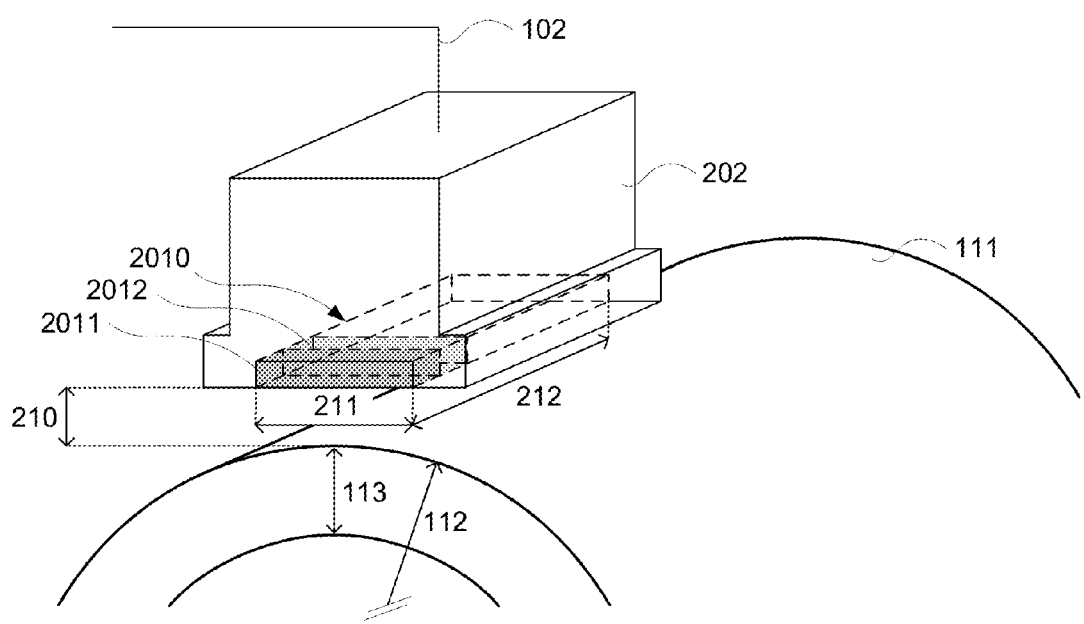
FIG. 2 is a schematic of a phased array probe, free of the probe holder shown in FIG. 1, and arranged in the manner of the preferred embodiment over a cylindrical part to inspect.

A phased array probe enclosed inside the probe holder 101 is presented in FIG. 2 together with a section of an inspected cylindrical part 111 (depicted is a tube section). The transducer array 2010 embedded within the probe housing 202 is electronically reached through the uplink 203, itself connected to the acquisition device 104. The array itself is composed of columns of transducers such as 2011 and 2012 along the scan axis 212. The perpendicular axis to the scan axis is the elevation axis 211. According to the preferred embodiment, the elevation axis is perpendicular to the cylindrical part axis, whereas the scan axis is parallel to the cylindrical part axis. The challenge that is met by the present method according to the preferred embodiment is to adapt the acoustic beam formed along the elevation axis 211 by each column of transducers 2011, 2012, . . . to the cylindrical part diameter 112 and near-surface inspection range 113 given a constant probe-to-part distance 210. The volume separating the probe within the probe holder and the cylindrical part surface is filled with an appropriate acoustic coupling material.

Figure 3:
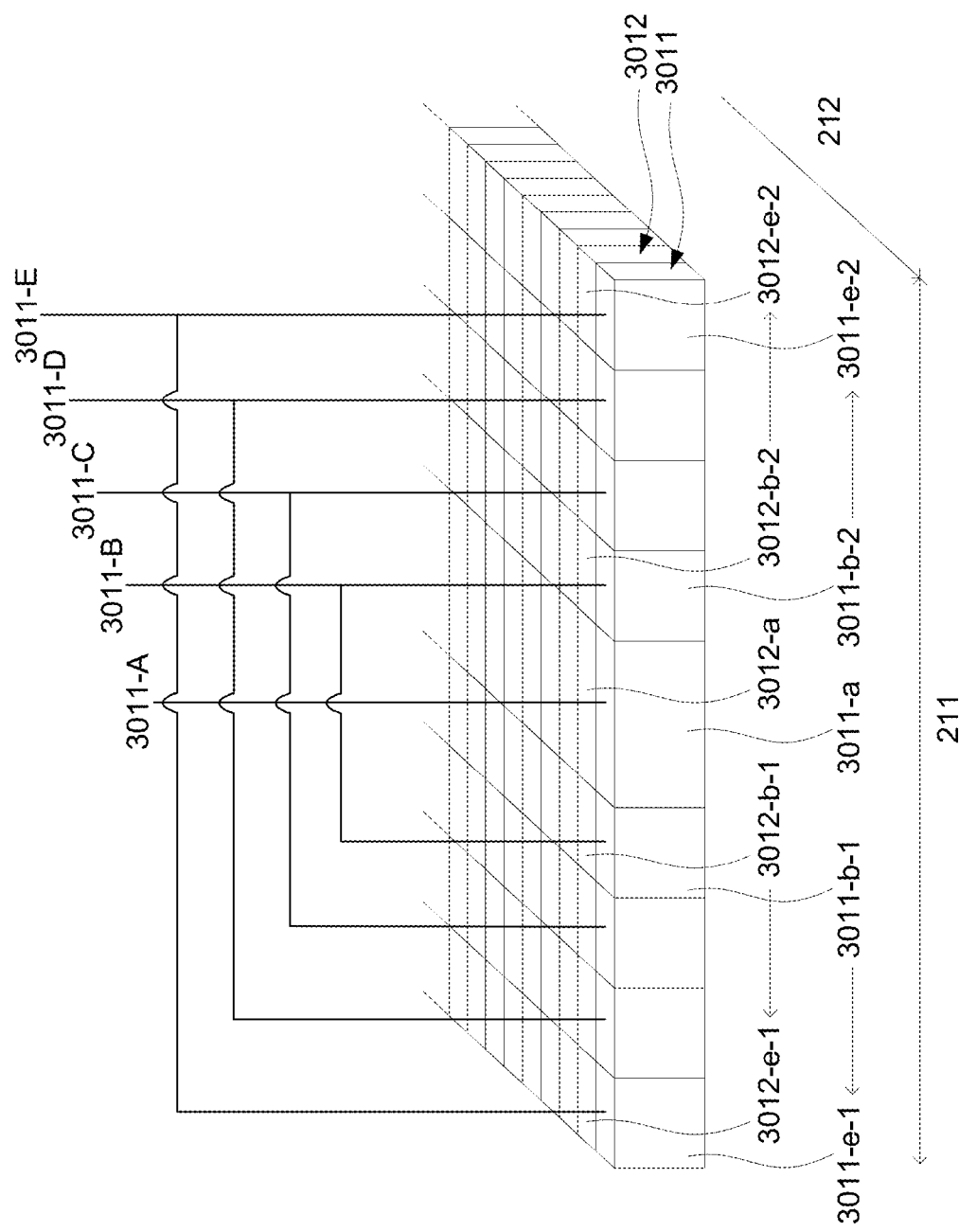
FIG. 3 is a schematic of a 9×N elemental transducers array in a 1.5 D configuration as found under the configuration of FIG. 2.

The present method makes use of a 1.5D array of transducers, a section of which is schematically represented on FIG. 3, to achieve the fore mentioned objective. This array comprise a matrix of individual transducers 3011-*a*, 3011-*b*-1, 3011-*b*-2 . . . 3012-*a*, 3012-*b*-1, 3012-*b*-2 . . . along the rows of the elevation axis 211 and the columns 3011, 3012 . . . along the scan axis 212. In each column, say column 3011, the elemental transducers are electronically grouped in pairs 3011-*b*-1 and 3011-*b*-2, . . . , 3011-*e*-1 and 3011-*e*-2 through the leads 3011-B, . . . , 3011-E respectively. Only the center element 3011-*a* has its own lead 3011-A. The transducer array may possess any number of rows or columns: FIG. 3 depicts an array of 9 rows only for the sake of illustration.

Figure 4:
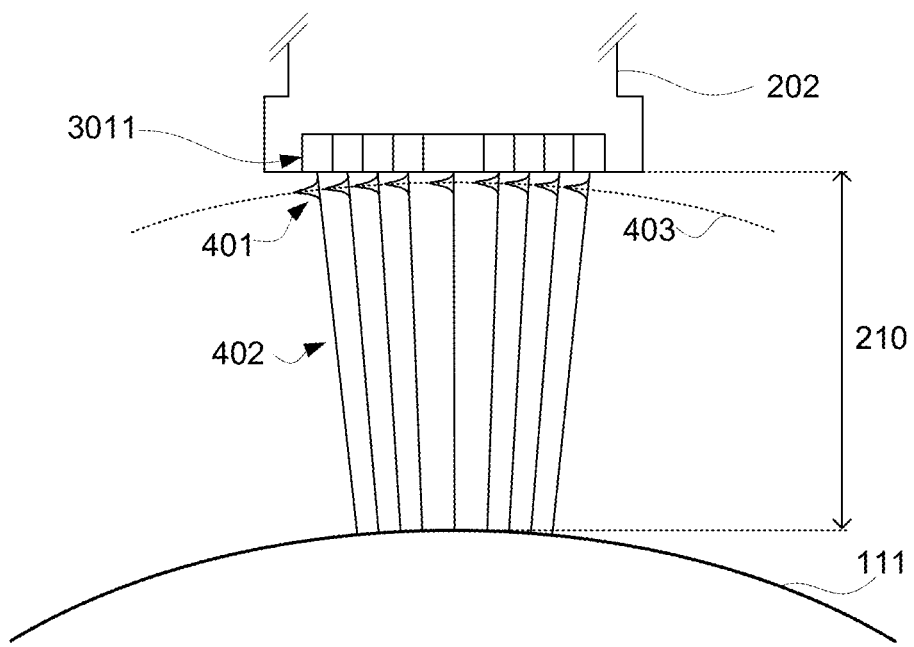
FIG. 4 is a schematic cross section view along the elevation axis of one column of transducers found in FIG. 3 of the concentric firing pattern put forward by the preferred.

With regards to the preferred embodiment, the 1.5D array is operated using two collaborating effects. The first one is the on-time arrival on the cylindrical part surface of the pulsed acoustic field emitted from every elemental transducer. This effect is related to the firing pattern as presented on FIG. 4 where a common cross section of the probe housing 202, of the transducer array at the level of column 3011, and of the cylindrical part 111 is presented. The firing sequence of a column of transducers is triggered as to form a series of acoustic pulses 401 that fall on a common arc of circle 403 positioned at the same minimum time of flight from the cylindrical part surface 402. Thus, the arc of circle 403 is concentrical to the cylindrical part 111 and is thereof adapted to the probe-to-part distance 210. This in turn is done by activating with adequate time delays the elements of the array through the electronic leads 3011-A, . . . , 3011-E of FIG. 3. Following this configuration, since the pulsed acoustic field arrives simultaneously in time at the cylindrical bar interface, the front wall reflection echo reaches the probe with the same delays as the ones used for building the concentric firing pattern. This accounts for the sharp and coherent front wall reflection echo.

Figure 5:
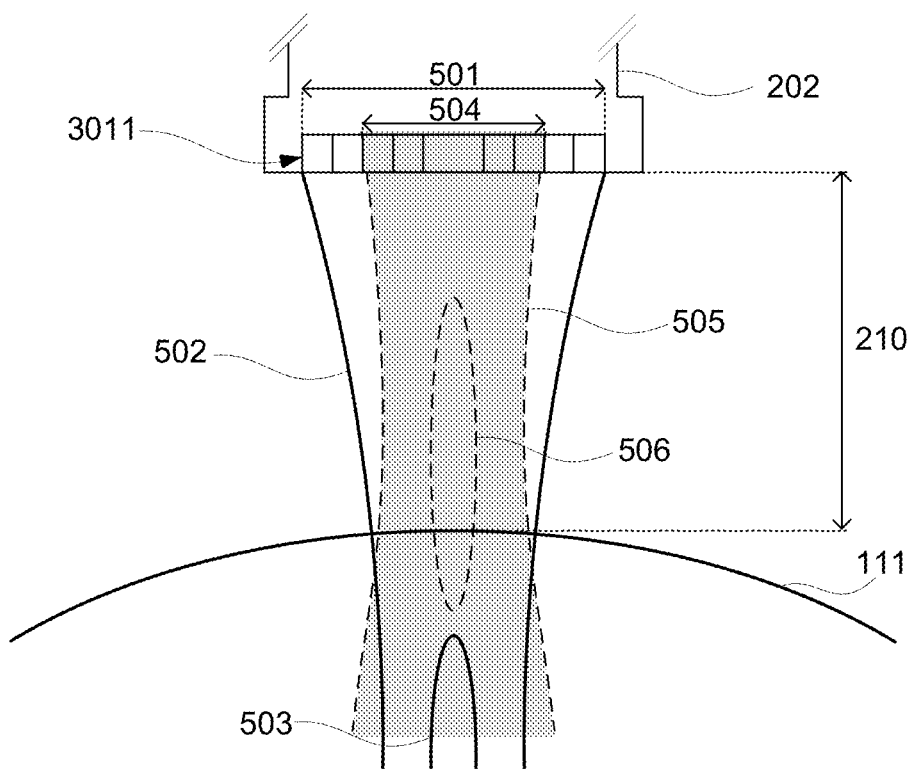
FIG. 5 is a schematic cross section view along the elevation axis of one column of transducers found in FIG. 3 of the time average envelope of the acoustic field for two aperture sizes.

The second effect to consider is the impact of the probe aperture size on the intensity profile of the acoustic field. A conceptual representation of this is shown on FIG. 5 where a common cross section of the probe housing 202, of the enclosed array at the level of column 3011, and of the cylindrical part 111 is presented. Given a firing sequence such as the one depicted in FIG. 4, for a full width aperture size 501, the envelope of the time averaged forward propagating acoustic field 502 has a maximum (modulus of) intensity distribution 503 at the farthest achievable position from the probe. Any smaller aperture size, 504 for instance, produces a field envelope 505 whose maximum intensity distribution 506 is closer to the array. Given a probe-to-part distance 210, and a prescribed near surface inspection range 113 as seen on FIG. 2, it is feasible to optimize the (modulus of) acoustic field intensity deposited inside the concerned area, thereof augmenting the signal-noise ratio of an eventual flaw inside the inspected region.

Figure 6:
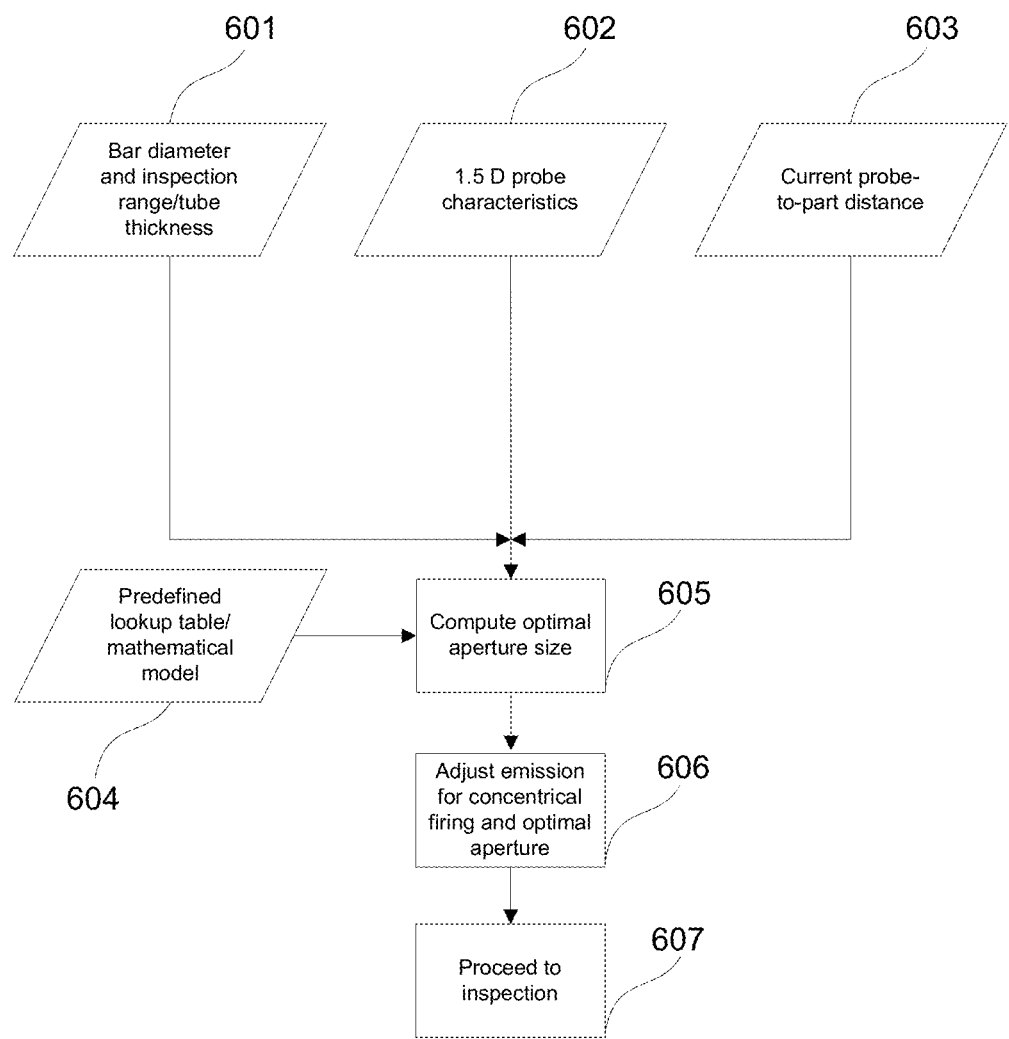
FIG. 6 is a flowchart of the method according to the preferred embodiment.

These two effects—firing in a concentric pattern and aperture adaptation—are combined to produce a sharp front wall echo with minimum extent and an improved signal to noise ratio on potential flaws within the near surface region. Since these settings are configurable by electronic means, the present method is suitable to carry out improved material inspection using a single mechanical configuration of the inspection system over both a range of cylindrical part diameters and a range of inspection domains. The overall method is summarized in the flowchart presented on FIG. 6. The main inputs for a successful implementation of the preferred embodiment are the cylindrical part diameter and intended range of inspection 601, the 1.5 D probe characteristics 602 and the current probe-to-part distance 603. These inputs are tested through a lookup table prefilled from empirical or simulated results, or through direct calculation 604 to determine the optimal aperture size for the intended inspection range 605. A concentric firing pattern is set and the optimal aperture size is selected accordingly 606, and the inspection of the near surface range of the cylindrical part according to the preferred embodiment may begin 607.

While this method has been particularly shown and described with respect to the preferred embodiment, it will be understood by those skilled in the art that various changes in form and details may be made without departing from the spirit and scope of the method. For instance, the combination of columns of elements adapted according to the preferred embodiment, but activated along the primary axis like common uni-dimensional PA probe to allow for beam steering or primary axis focusing is considered as another embodiment of the same method.

What is claimed is:

1. An ultrasonic inspection system configured to be coupled with a 1.5 D array acoustic probe, the probe including a plurality of transducers arranged in a linear bi-dimensional matrix and being engaged with a test surface of a cylindrical test object during the inspection of the test object, and the probe is operable by the system with an optimal size of aperture, the system comprises, an acquisition unit configured to execute desired focal laws to energize the probe to emit an acoustic field and receive corresponding response signals;

a data processing and control unit for analyzing and displaying inspection result based on the response signals, the processing and control unit further comprising, a probe control module providing a set of required inspection parameters pertaining to the cylindrical test object, an aperture optimization module providing the optimal size of the aperture according to the required inspection parameters, a concentric delay module providing delay-based concentric focal laws as the desired focal laws for the optimal aperture, and the desired focal laws are subsequently provided to the acquisition unit for energizing the probe.

2. The system of claim 1 is operable to provide the capacity of the inspection of the said test object based on a set of known probe characteristics, the required inspection parameters of the test object and the probe-to-test object distance.

3. The system of claim 2, wherein the aperture optimization module and the concentric delay module are configured to suit for the near surface inspection of the cylindrical test object with varying diameters without recurring need for mechanical adjustments of the probe-to-part distance.

4. The system of claim 1, wherein the acquisition module is configured so that the plurality of transducers are controlled to transmit an acoustic field in a way that the sound pulse from each transducer reaches the test surface simultaneously in time.

5. The system of claim 1, wherein the probe has an elevation axis and the aperture optimization module determines the size of the aperture along the elevation axis in a way so that the intensity of the acoustic field within the desired near surface inspection range is optimum.

6. The system of claim 1 further includes a user interface for displaying inspection results.

\* \* \* \* \*